(12) United States Patent
Hashitera et al.

(10) Patent No.: US 8,026,393 B2
(45) Date of Patent: Sep. 27, 2011

(54) SOFT-GELATIN CAPSULE FORMULATION

(75) Inventors: Yukiko Hashitera, Kobe (JP); Ryu Hirata, Sanda (JP); Yasuhiro Harada, Sanda (JP); Ryuji Ueno, Potomac, MD (US)

(73) Assignees: Sucampo AG, Zug (CH); R-Tech Ueno, Ltd., Tokyo (JP)

( * ) Notice: Subject to any disclaimer, the term of this patent is extended or adjusted under 35 U.S.C. 154(b) by 275 days.

(21) Appl. No.: 11/656,476

(22) Filed: Jan. 23, 2007

(65) Prior Publication Data
US 2007/0172523 A1  Jul. 26, 2007

Related U.S. Application Data

(60) Provisional application No. 60/761,360, filed on Jan. 24, 2006.

(51) Int. Cl.
*C07C 61/06* (2006.01)
*C07C 61/20* (2006.01)

(52) U.S. Cl. .................................. 562/504; 514/513

(58) Field of Classification Search .................. None
See application file for complete search history.

(56) References Cited

U.S. PATENT DOCUMENTS

| | | | |
|---|---|---|---|
| 4,755,531 A * | 7/1988 | Muchowski et al. ....... 514/513 |
| 4,780,316 A * | 10/1988 | Brox .......................... 424/456 |
| 5,073,569 A | 12/1991 | Ueno et al. | |
| 5,106,869 A | 4/1992 | Ueno et al. | |
| 5,166,174 A | 11/1992 | Ueno et al. | |
| 5,212,324 A | 5/1993 | Ueno | |
| 5,221,763 A | 6/1993 | Ueno et al. | |
| 5,225,439 A | 7/1993 | Ueno et al. | |
| 5,284,858 A | 2/1994 | Ueno et al. | |
| 5,317,032 A | 5/1994 | Ueno et al. | |
| 5,380,709 A | 1/1995 | Ueno et al. | |
| 5,428,062 A | 6/1995 | Ueno et al. | |
| 5,534,547 A | 7/1996 | Ueno et al. | |
| 5,591,887 A | 1/1997 | Ueno et al. | |
| 5,739,161 A | 4/1998 | Ueno | |
| 5,770,759 A | 6/1998 | Ueno et al. | |
| 5,886,034 A | 3/1999 | Ueno et al. | |
| 5,998,438 A * | 12/1999 | Slassi et al. ................ 514/316 |
| 6,207,699 B1 * | 3/2001 | Rothman ...................... 514/419 |
| 6,242,485 B1 | 6/2001 | Ueno | |
| 6,265,440 B1 | 7/2001 | Ueno et al. | |
| 6,583,174 B1 | 6/2003 | Ueno et al. | |

FOREIGN PATENT DOCUMENTS

| | | |
|---|---|---|
| EP | 0 415 564 A2 | 3/1991 |
| EP | 1 362 588 A | 11/2003 |
| WO | WO 01/27099 A2 | 4/2001 |
| WO | WO 2005/002588 A | 1/2005 |

* cited by examiner

*Primary Examiner* — Daniel Sullivan
*Assistant Examiner* — Yevegeny Valenrod
(74) *Attorney, Agent, or Firm* — Sughrue Mion, PLLC

(57) ABSTRACT

The present invention discloses a soft gelatin capsule formulation of a 15-keto-prostaglandin compound, which comprises: a soft gelatin capsule shell comprising gelatin and sugar alcohol as a plasticizer, and a mixture comprising a 15-keto-prostaglandin compound and a pharmaceutically acceptable vehicle which is filled in the shell. By encapsulating the 15-keto-prostaglandin compound in the specified soft gelatin capsule shell, stability of the compound is significantly improved.

22 Claims, No Drawings

SOFT-GELATIN CAPSULE FORMULATION

CROSS REFERENCE TO RELATED APPLICATION

This application claims the benefit of U.S. Provisional Application No. US60/761,360 filed Jan. 24, 2006.

FIELD OF THE INVENTION

The present invention relates to a soft-gelatin capsule formulation of a therapeutically effective 15-keto-prostaglandin compound.

BACKGROUND ART

Prostaglandins (hereinafter, referred to as PGs) are members of class of organic carboxylic acids, which are contained in tissues or organs of human and other mammals, and exhibit a wide range of physiological activities. PGs found in nature (primary PGs) have, as a general structural property thereof, a prostanoic acid skeleton as shown in the formula (A):

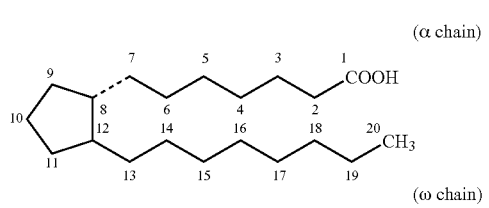

On the other hand, some synthetic analogues have modified skeletons. The primary PGs are classified into PGAs, PGBs, PGCs, PGDs, PGEs, PGFs, PGGs, PGHs, PGIs and PGJs on the basis of the structural property of the five membered ring moiety, and further classified into the following three types by the number and position of the unsaturated bond in the carbon chain moiety.

Type 1 (subscript 1): 13,14-unsaturated-15-OH
Type 2 (subscript 2): 5,6- and 13,14-diunsaturated-15-OH
Type 3 (subscript 3): 5,6-, 13,14-, and 17,18-triunsaturated-15-OH.

Further, PGFs are classified on the basis of the configuration of the hydroxyl group at the 9-position into a type (wherein the hydroxyl group is of the α-configuration) and β type (wherein the hydroxyl group is of the β-configuration).

In addition, some 15-keto-PGs (PGs having an oxo group at position 15 in place of the hydroxy group) and 13,14-dihydro-15-keto-PGs have been known as substances naturally produced by enzymatic actions during metabolism of the primary PGs and have some therapeutic effect. 15-keto-PGs have been disclosed in U.S. Pat. Nos. 5,073,569, 5,534,547, 5,225,439, 5,166,174, 5,428,062 5,380,709 5,886,034 6,265,440, 5,106,869, 5,221,763, 5,591,887, 5,770,759 and 5,739,161. The contents of these publications are herein incorporated by reference.

For example, 15-keto-16-halogen prostaglandin compounds are useful as cathartics (U.S. Pat. No. 5,317,032, the contents of the reference is herein incorporated by reference). For treating gastrointestinal diseases, the agent is preferably formulated as an orally administrable dosage form. In general, PG compounds are less soluble in water and become significantly unstable under the presence of water. A capsulated formulation comprises a 15-keto-16-halogen PG compound and a solvent which can maintain the stability of the compound such as glyceride had been proposed (WO01/027099 (U.S. Pat. No. 6,583,174), the contents of the cited reference is herein incorporated by reference.

Elastic shell of a soft gelatin capsule, in general, incorporates a plasticizer in addition to gelatin. Examples of plasticizer include glycerin, propylene glycol, sorbitol, maltitol, sugar alcohol solution derived from corn starch (Anidrisorb™, Polysorb™), i.e. a mixture of sorbitol, sorbitane, mannitol and hydrogenated starch hydrolysate, hydrogenated maltose starch syrup, i.e. a mixture of maltitol, sorbitol and oligosaccharide alcohol.

SUMMARY OF THE INVENTION

An object of the present invention is to provide an orally administrable dosage form of a 15-keto-prostaglandin compound which has an excellent shelf stability.

Accordingly, the instant application provides a soft gelatin capsule formulation of a 15-keto-prostaglandin compound, which comprises:

a soft gelatin capsule shell comprising gelatin and a sugar alcohol as a plasticizer, and a mixture comprising a 15-keto-prostaglandin compound and a pharmaceutically acceptable vehicle, which is filled in the shell.

The invention is also provides a method for improving stability of a 15-keto-prostaglandin compound which comprises, dissolving the 15-keto-prostaglandin in a pharmaceutically acceptable solvent and incorporating the solution in a soft-gelatin capsule whose shell comprises gelatin and a sugar alcohol as a plasticizer.

DETAILED DESCRIPTION OF THE PREFERRED EMBODIMENTS

The nomenclature of the PG compounds used herein is based on the numbering system of prostanoic acid represented in the above formula (A).

The formula (A) shows a basic skeleton of the C-20 PG compound, but the present invention is not limited to those having the same number of carbon atoms. In the formula (A), the numbering of the carbon atoms which constitute the basic skeleton of the PG compounds starts at the carboxylic acid (numbered 1), and carbon atoms in the α-chain are numbered 2 to 7 towards the five-membered ring, those in the ring are 8 to 12, and those in the ω-chain are 13 to 20. When the number of carbon atoms is decreased in the α-chain, the number is deleted in the order starting from position 2; and when the number of carbon atoms is increased in the α-chain, compounds are named as substitution compounds having respective substituents at position 2 in place of carboxy group (C-1). Similarly, when the number of carbon atoms is decreased in the ω-chain, the number is deleted in the order starting from position 20; and when the number of carbon atoms is increased in the ω-chain, compounds are named as substitution compounds having respective substituents at position 20. Stereochemistry of the compounds is the same as that of the above formula (A) unless otherwise specified.

In general, each of PGD, PGE and PGF represents a PG compound having hydroxy groups at positions 9 and/or 11, but in the present specification and claims they also include those having substituents other than the hydroxyl groups at positions 9 and/or 11. Such compounds are referred to as 9-dehydroxy-9-substituted-PG compounds or 11-dehydroxy-11-substituted-PG compounds. A PG compound having hydrogen in place of the hydroxy group is simply named as 9- or 11-dehydroxy compound.

As stated above, the nomenclature of PG compounds is based on the prostanoic acid skeleton. However, in case the compound has a similar partial construction as a prostaglandin, the abbreviation of "PG" may be used. Thus, a PG compound of which α-chain is extended by two carbon atoms, that is, having 9 carbon atoms in the α-chain is named as 2-decarboxy-2-(2-carboxyethyl)-PG compound. Similarly, a PG compound having 11 carbon atoms in the α-chain is named as 2-decarboxy-2-(4-carboxybutyl)-PG compound. Further, a PG compound of which ω-chain is extended by two carbon atoms, that is, having 10 carbon atoms in the ω-chain is named as 20-ethyl-PG compound. These compounds, however, may also be named according to the IUPAC nomenclatures.

The 15-keto-PG compound used in the present invention may be any derivative of a PG insofar as having an oxo group at position 15 in place of the hydroxy group, and may further include a compound having one double bond between positions 13 and 14 (15-keto-PG type 1 compound), two double bonds between positions 13 and 14, and positions 5 and 6 (15-keto-PG type 2 compound), and three double bonds between positions 5 and 6, positions 13 and 14, and positions 17 and 18 (15-keto-PG type 3 compound), and a derivative thereof wherein the bond between the positions 13 and 14 is single bond, in place of the double bond (13,14-dihydro-15-keto-PG compound).

Examples of the analogue including substitution compounds or derivatives include a PG compound of which the carboxy group at the end of the alpha chain is esterified; physiologically acceptable salt thereof; an unsaturated derivative having a double bond between positions 2 and 3 or a triple bond between positions 5 and 6; PG compounds having substituent(s) on carbon atom(s) at position(s) 3, 5, 6, 16, 17, 18, 19 and/or 20; and PG compounds having lower alkyl or a hydroxy (lower) alkyl group at position 9 and/or 11 in place of the hydroxy group.

According to the present invention, preferred substituents on the carbon atom at position(s) 3, 17, 18 and/or 19 include alkyl having 1 to 6 carbon atoms, especially methyl and ethyl. Preferred substituents on the carbon atom at position 16 include lower alkyl such as methyl and ethyl, hydroxy, halogen atom such as chlorine and fluorine, and aryloxy such as trifluoromethylphenoxy. Preferred substituents on the carbon atom at position 17 include halogen atom such as chlorine and fluorine. Preferred substituents on the carbon atom at position 20 include saturated or unsaturated lower alkyl such as $C_{1-4}$ alkyl, lower alkoxy such as $C_{1-4}$ alkoxy, and lower alkoxy alkyl such as $C_{1-4}$ alkoxy-$C_{1-4}$ alkyl. Preferred substituents on the carbon atom at position 5 include halogen atoms such as chlorine and fluorine. Preferred substituents on the carbon atom at position 6 include an oxo group forming a carbonyl group. Stereochemistry of PGs having hydroxy, lower alkyl or hydroxy(lower)alkyl substituent on the carbon atom at positions 9 and 11 may be α, β or a mixture thereof.

Further, the above described derivatives may have a ω chain shorter than that of the primary PGs and a substituent such as alkoxy, cyclohexyl, cyclohexyloxy, phenoxy and phenyl at the end of the truncated ω-chain.

Especially preferred compounds include a 13,14-dihydro-15-keto-PG compound that has a single bond between positions 13 and 14; a 15-keto-16-mono or 16,16-di-halogen PG compound that has at least one halogen atom, especially fluorine, at carbon atom of position 16; a 15-keto-PGE compound that has hydroxy group at position 9 and oxo group at position 11 of the five membered ring.

A preferred prostaglandin compound used in the is present invention is represented by the formula (I):

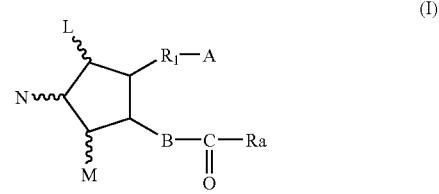

wherein L, M and N are hydrogen, hydroxy, halogen, lower alkyl, hydroxy(lower)alkyl, lower alkanoyloxy or oxo, wherein at least one of L and M is a group other than hydrogen, and the five-membered ring may have at least one double bond;
A is —$CH_3$, or —$CH_2OH$, —$COCH_2OH$, —$COOH$ or a functional derivative thereof;
B is —$CH_2$—$CH_2$—, —CH=CH— or —C≡C—;
$R_1$ is a saturated or unsaturated bivalent lower or medium aliphatic hydrocarbon residue, which is unsubstituted or substituted with halogen, lower alkyl, hydroxy, oxo, aryl or heterocyclic group, and at least one of carbon atom in the aliphatic hydrocarbon is optionally substituted by oxygen, nitrogen or sulfur; and
Ra is a saturated or unsaturated lower or medium aliphatic hydrocarbon residue, which is unsubstituted or substituted with halogen, oxo, hydroxy, lower alkyl, lower alkoxy, lower alkanoyloxy, cyclo(lower)alkyl, cyclo(lower)alkyloxy, aryl, aryloxy, heterocyclic group or heterocyclicoxy group; lower alkoxy; lower alkanoyloxy; cyclo(lower)alkyl; cyclo(lower)alkyloxy; aryl; aryloxy; heterocyclic group; heterocyclicoxy group.

A more preferred prostaglandin compound used in the present invention is represented by the formula (II):

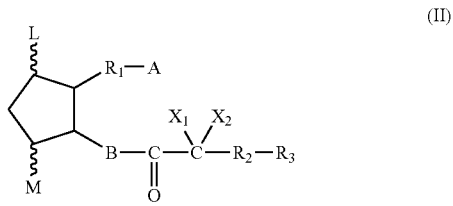

wherein L and M are hydrogen, hydroxy, halogen, lower alkyl, hydroxy(lower)alkyl, lower alkanoyloxy or oxo, wherein at least one of L and M is a group other than hydrogen, and the five-membered ring may have one or more double bonds;
A is —$CH_3$, or —$CH_2OH$, —$COCH_2OH$, —$COOH$ or a functional derivative thereof;
B is —$CH_2$—$CH_2$—, —CH=CH— or —C≡C—;
$X_1$ and $X_2$ are hydrogen, lower alkyl, or halogen;
$R_1$ is a saturated or unsaturated bivalent lower or medium aliphatic hydrocarbon residue, which is unsubstituted or substituted with halogen, lower alkyl, hydroxy, oxo, aryl or heterocyclic group, and at least one of carbon atom in the aliphatic hydrocarbon is optionally substituted by oxygen, nitrogen or sulfur;
$R_2$ is a single bond or lower alkylene; and
$R_3$ is lower alkyl, lower alkoxy, lower alkanoyloxy, cyclo(lower)alkyl, cyclo(lower)alkyloxy, aryl, aryloxy, heterocyclic group or heterocyclicoxy group.

In the above formula, the term "unsaturated" in the definitions for $R_1$ and Ra is intended to include at least one or more double bonds and/or triple bonds that are isolatedly, separately or serially present between carbon atoms of the main and/or side chains. According to the usual nomenclature, an unsaturated bond between two serial positions is represented by denoting the lower number of the two positions, and an unsaturated bond between two distal positions is represented by denoting both of the positions.

The term "lower or medium aliphatic hydrocarbon" refers to a straight or branched chain hydrocarbon group having 1 to 14 carbon atoms (for a side chain, 1 to 3 carbon atoms are preferable) and preferably 1 to 10, especially 6 to 10 carbon atoms for $R_1$ and 1 to 10, especially, 1 to 8 carbon atoms for Ra.

The term "halogen" covers fluorine, chlorine, bromine and iodine.

The term "lower" is intended to include a group having 1 to 6 carbon atoms unless otherwise specified.

The term "lower alkyl" refers to a straight or branched chain saturated hydrocarbon group containing 1 to 6 carbon atoms and includes, for example, methyl, ethyl, propyl, isopropyl, butyl, isobutyl, sec-butyl, t-butyl, pentyl and hexyl.

The term "lower alkoxy" refers to a group of lower alkyl-O—, wherein lower alkyl is as defined above.

The term "hydroxy(lower)alkyl" refers to a lower alkyl as defined above which is substituted with at least one hydroxy group such as hydroxymethyl, 1-hydroxyethyl, 2-hydroxyethyl and 1-methyl-1-hydroxyethyl.

The term "lower alkanoyloxy" refers to a group represented by the formula RCO—O—, wherein RCO— is an acyl group formed by oxidation of a lower alkyl group as defined above, such as acetyl.

The term "cyclo(lower)alkyl" refers to a cyclic group formed by cyclization of a lower alkyl group as defined above but contains three or more carbon atoms, and includes, for example, cyclopropyl, cyclobutyl, cyclopentyl and cyclohexyl.

The term "cyclo(lower)alkyloxy" refers to the group of cyclo(lower)alkyl-O—, wherein cyclo(lower)alkyl is as defined above.

The term "aryl" may include unsubstituted or substituted aromatic hydrocarbon rings (preferably monocyclic groups), for example, phenyl, tolyl, xylyl. Examples of the substituents are halogen atom and halo(lower)alkyl, wherein halogen atom and lower alkyl are as defined above.

The term "aryloxy" refers to a group represented by the formula ArO—, wherein Ar is aryl as defined above.

The term "heterocyclic group" may include mono- to tricyclic, preferably monocyclic heterocyclic group which is 5 to 14, preferably 5 to 10 membered ring having optionally substituted carbon atom and 1 to 4, preferably 1 to 3 of 1 or 2 type of hetero atoms selected from nitrogen, oxygen and sulfur. Examples of the heterocyclic group include furyl, thienyl, pyrrolyl, oxazolyl, isoxazolyl, thiazolyl, isothiazolyl, imidazolyl, pyrazolyl, furazanyl, pyranyl, pyridyl, pyridazinyl, pyrimidyl, pyrazinyl, 2-pyrrolinyl, pyrrolidinyl, 2-imidazolinyl, imidazolidinyl, 2-pyrazolinyl, pyrazolidinyl, piperidino, piperazinyl, morpholino, indolyl, benzothienyl, quinolyl, isoquinolyl, purinyl, quinazolinyl, carbazolyl, acridinyl, phenanthridinyl, benzimidazolyl, benzimidazolinyl, benzothiazolyl, phenothiazinyl. Examples of the substituent in this case include halogen, and halogen substituted lower alkyl group, wherein halogen atom and lower alkyl group are as described above.

The term "heterocyclicoxy group" means a group represented by the formula HcO—, wherein Hc is a heterocyclic group as described above.

The term "functional derivative" of A includes salts, preferably pharmaceutically acceptable salts, ethers, esters and amides.

Suitable "pharmaceutically acceptable salts" include salts formed with non-toxic bases conventionally used in pharmaceutical field, for example a salt with an inorganic base such as an alkali metal salt (such as sodium salt and potassium salt), an alkaline earth metal salt (such as calcium salt and magnesium salt), an ammonium salt; or a salt with an organic base, for example, an amine salt including such as methylamine salt, dimethylamine salt, cyclohexylamine salt, benzylamine salt, piperidine salt, ethylenediamine salt, ethanolamine salt, diethanolamine salt, triethanolamine salt, tris(hydroxymethylamino)ethane salt, monomethylmonoethanolamine salt, procaine salt and caffeine salt), a basic amino acid salt (such as arginine salt and lysine salt), tetraalkyl ammonium salt and the like. These salts may be prepared by a conventional process, for example from the corresponding acid and base or by salt interchange.

Examples of the ethers include alkyl ethers, for example, lower alkyl ethers such as methyl ether, ethyl ether, propyl ether, isopropyl ether, butyl ether, isobutyl ether, t-butyl ether, pentyl ether and 1-cyclopropyl ethyl ether; and medium or higher alkyl ethers such as octyl ether, diethylhexyl ether, lauryl ether and cetyl ether; unsaturated ethers such as oleyl ether and linolenyl ether; lower alkenyl ethers such as vinyl ether, allyl ether; lower alkynyl ethers such as ethynyl ether and propynyl ether; hydroxy(lower)alkyl ethers such as hydroxyethyl ether and hydroxyisopropyl ether; lower alkoxy (lower)alkyl ethers such as methoxymethyl ether and 1-methoxyethyl ether; optionally substituted aryl ethers such as phenyl ether, tosyl ether, t-butylphenyl ether, salicyl ether, 3,4-di-methoxyphenyl ether and benzamidophenyl ether; and aryl(lower)alkyl ethers such as benzyl ether, trityl ether and benzhydryl ether.

Examples of the esters include aliphatic esters, for example, lower alkyl esters such as methyl ester, ethyl ester, propyl ester, isopropyl ester, butyl ester, isobutyl ester, t-butyl ester, pentyl ester and 1-cyclopropylethyl ester; lower alkenyl esters such as vinyl ester and allyl ester; lower alkynyl esters such as ethynyl ester and propynyl ester; hydroxy(lower) alkyl ester such as hydroxyethyl ester; lower alkoxy (lower) alkyl esters such as methoxymethyl ester and 1-methoxyethyl ester; and optionally substituted aryl esters such as, for example, phenyl ester, tolyl ester, t-butylphenyl ester, salicyl ester, 3,4-di-methoxyphenyl ester and benzamidophenyl ester; and aryl(lower)alkyl ester such as benzyl ester, trityl ester and benzhydryl ester.

The amide of A means a group represented by the formula —CONR'R", wherein each of R' and R" is hydrogen, lower alkyl, aryl, alkyl- or aryl-sulfonyl, lower alkenyl and lower alkynyl, and include for example lower alkyl amides such as methylamide, ethylamide, dimethylamide and diethylamide; arylamides such as anilide and toluidide; and alkyl- or arylsulfonylamides such as methylsulfonylamide, ethylsulfonylamide and tolylsulfonylamide.

Preferred examples of L and M include hydroxy and oxo, and especially, M is hydroxy and L is oxo which has a 5-membered ring structure of, so called, PGE type.

Preferred example of A is —COOH, its pharmaceutically acceptable salt, ester or amide thereof.

Preferred example of B is —CH$_2$—CH$_2$—, which provide the structure of so-called, 13,14-dihydro type.

Preferred example of $X_1$ and $X_2$ is that at least one of them is halogen, more preferably, both of them are halogen, especially, fluorine that provides a structure of, so called 16,16-difluoro type.

Preferred $R_1$ is a hydrocarbon residue containing 1-10 carbon atoms, preferably 6 to 10 carbon atoms. Further, at least one carbon atom in the aliphatic hydrocarbon is optionally substituted by oxygen, nitrogen or sulfur.

Examples of $R_1$ include, for example, the following groups:

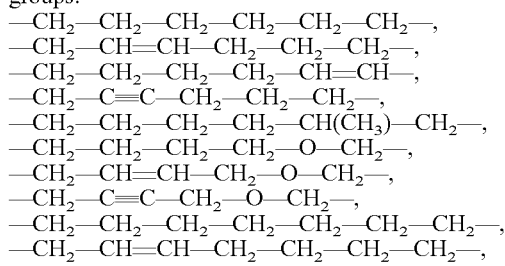

—CH$_2$—CH$_2$—CH$_2$—CH$_2$—CH$_2$—CH=CH—,
—CH$_2$—C≡C—CH$_2$—CH$_2$—CH$_2$—CH$_2$—,
—CH$_2$—CH$_2$—CH$_2$—CH$_2$—CH$_2$—CH(CH$_3$)—CH$_2$—,
—CH$_2$—CH$_2$—CH$_2$—CH$_2$—CH$_2$—CH$_2$—CH$_2$—CH$_2$—,
—CH$_2$—CH=CH—CH$_2$—CH$_2$—CH$_2$—CH$_2$—CH$_2$—,
—CH$_2$—CH$_2$—CH$_2$—CH$_2$—CH$_2$CH$_2$—CH=CH—,
—CH$_2$—C≡C—CH$_2$—CH$_2$—CH$_2$—CH$_2$—CH$_2$—, and
—CH$_2$—CH$_2$—CH$_2$—CH$_2$—CH$_2$—CH$_2$—CH(CH$_3$)—CH$_2$—.

Preferred Ra is a hydrocarbon containing 1 to 10 carbon atoms, more preferably, 1 to 8 carbon atoms. Ra may have one or two side chains having one carbon atom.

The configuration of the ring and the α- and/or ω chains in the above formula (I) and (II) may be the same as or different from that of the primary PGs. However, the present invention also includes a mixture of a compound having a primary type configuration and a compound of a non-primary type configuration.

The typical example of the present compounds are 13,14-dihydro-15-keto-16-mono- or 16,16-di-fluoro PGE compound and its derivative or analogue.

In the present invention, the 15-keto-PG compound may be in the keto-acetal equilibrium by formation of a hemiacetal between hydroxy at position 11 and keto at position 15.

For example, it has been revealed that when both of $X_1$ and $X_2$ are halogen atoms, especially, fluorine atoms, the compound contains a tautomeric isomer, bi-cyclic compound.

If such tautomeric isomers as above are present, the proportion of both tautomeric isomers varies with the structure of the rest of the molecule or the kind of the substituent present. Sometimes one isomer may predominantly be present in comparison with the other. However, it is to be appreciated that the present invention includes both isomers.

Further, the 15-keto-PG compounds used in the invention include the bi-cyclic compound and analogs or derivatives thereof.

The bi-cyclic compound is represented by the formula (III):

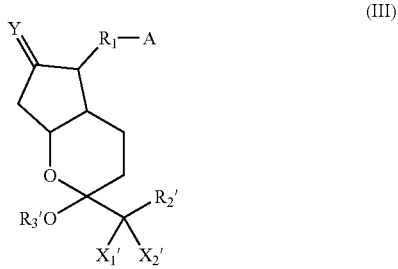

(III)

wherein, A is —CH$_3$, or —CH$_2$OH, —COCH$_2$OH, —COOH or a functional derivative thereof;

$X_1'$ and $X_2'$ are hydrogen, lower alkyl, or halogen;

Y is

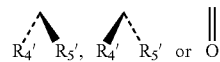

wherein $R_4'$ and $R_5'$ are hydrogen, hydroxy, halogen, lower alkyl, lower alkoxy or hydroxy(lower)alkyl, wherein $R_4'$ and $R_5'$ are not hydroxy and lower alkoxy at the same time;

$R_1$ is a saturated or unsaturated bivalent lower or medium aliphatic hydrocarbon residue, which is unsubstituted or substituted with halogen, lower alkyl, hydroxy, oxo, aryl or heterocyclic group, and at least one of carbon atom in the aliphatic hydrocarbon is optionally substituted by oxygen, nitrogen or sulfur;

$R_2'$ is a saturated or unsaturated lower or medium aliphatic hydrocarbon residue, which is unsubstituted or substituted with halogen, oxo, hydroxy, lower alkyl, lower alkoxy, lower alkanoyloxy, cyclo(lower)alkyl, cyclo(lower)alkyloxy, aryl, aryloxy, heterocyclic group or heterocyclicoxy group; lower alkyl; lower alkoxy; lower alkanoyloxy; cyclo(lower)alkyl; cyclo(lower)alkyloxy; aryl; aryloxy; heterocyclic group; heterocyclicoxy group; and $R_3'$ is hydrogen, lower alkyl, cyclo(lower)alkyl, aryl or heterocyclic group.

Furthermore, while the compounds used in the invention may be represented by a formula or name based on keto-type regardless of the presence or absence of the isomers, it is to be noted that such structure or name does not intend to exclude the acetal type compound.

In the present invention, any of isomers such as the individual tautomeric isomers, the mixture thereof, or optical isomers, the mixture thereof, a racemic mixture, and other steric isomers may be used in the same purpose.

Some of the compounds used in the present invention may be prepared by the method disclosed in U.S. Pat. Nos. 5,073,569, 5,166,174, 5,221,763, 5,212,324, 5,739,161 and 6,242,485, the contents of these references are herein incorporated by reference.

It has been known that 13,14-dihydro-15-keto-prostaglandin compound having the formula as shown below (Tautomer I) may be in equilibrium with its tautomeric isomer (tautomer II) (See U.S. Pat. No. 5,166,174, U.S. Pat. No. 5,225,439, U.S. Pat. No. 5,284,858, U.S. Pat. No. 5,380,709, U.S. Pat. No. 5,428,062 and U.S. Pat. No. 5,886,034, the contents of these references are herein incorporated by reference.)

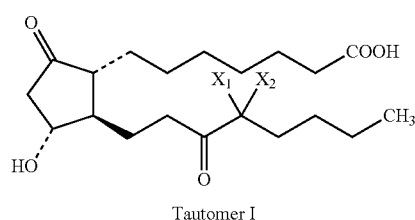

Tautomer I

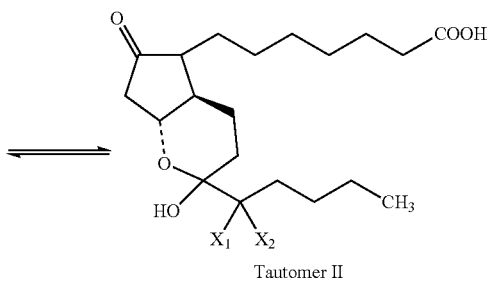

Tautomer II

It is considered that the halogen atom(s) at $X_1$ and/or $X_2$ promote bi-cyclic ring formation, such as the compound 1 or 2 below. In addition, in the absence of water, the tautomeric compounds as above exist predominantly in the form of the bi-cyclic compound. In aqueous media, it is supposed that hydrogen bonding occurs between the water molecule and, for example, the keto group on the hydrocarbon chain, thereby hindering bi-cyclic ring formation. The bi-cyclic/mono-cyclic structures, for example, may be present in a ratio of 6:1 in $D_2O$; 10:1 in $CD_3OD$-$D_2O$ and 96:4 in $CDCl_3$. In the instant specification and claims, tautomeric mixture containing the bi-cyclic compound in a ratio even greater to substantially 100% bi-cyclic compound is within this invention.

Embodiment of the bi-cyclic compound of the present invention include the Compounds 1 and 2 shown below.

Compound 1:

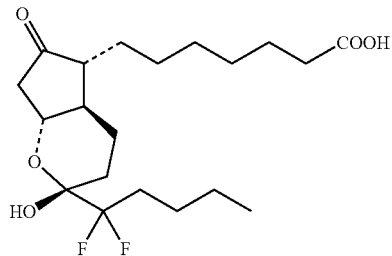

7-[(2R,4aR,5R,7aR)-2-(1,1-difluoropentyl)-2-hydroxy-6-oxooctahydrocyclopenta[b]pyran-5-yl]heptanoic acid Compound 2:

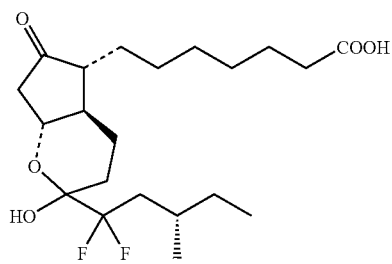

7-{(4aR,5R,7aR)-2-[(3S)-1,1-difluoro-3-methylpentyl]-2-hydroxy-6-oxooctahydrocyclopenta[b]pyran-5-yl}heptanoic acid According to the present invention, the pharmaceutically acceptable vehicle is not specifically limited as long as the vehicle can disperse the 15-keto-PG therein and does not significantly deteriorate the stability of the compound. In view of manufacturing soft gelatin capsule formulation, a solvent which is liquid at the room temperature. A solution, dispersion or mixture of the 15-keto-PG in the solvent may be filled in the capsule.

Examples of the pharmaceutically acceptable vehicles preferably used in the instant invention may be fatty acid esters, i.e. an ester of fatty acid and an alcohol, and polyols.

Preferred fatty acid which consists the fatty acid ester is a medium or higher chain fatty acid having at least C6, preferably C6-24 carbon atoms, for example caproic acid (C6), caprylic acid (C8), capric acid (C10), lauric acid (C12) and myristic acid (C14), palmitic acid (C16), palmitoleic acid (C16), stearic acid (C18), oleic acid (C18), linoleic acid (C18), linolenic acid (C18), ricinolic acid (C18) and arachic acid (C20). Preferred alcohols which consists the fatty acid ester may comprise C1-6 monovalent alcohol and polyols such as glycerin, polyethylene glycol and propylene glycol.

Preferred fatty acid esters may include a glyceride of a saturated or unsaturated fatty acid which may have a branched chain and a propylene glycol fatty acid ester. Two or more glycerides may be used as a mixture.

Examples of the mixture of glycerides are mixture of caprylic acid triglyceride and capric acid triglyceride, vegetable oils such as castor oil, corn oil, olive oil, sesame oil, rape oil, salad oil, cottonseed oil, camellia oil, peanut oil, palm oil and sunflower oil.

A fatty acid ester derived from a fatty acid and a monovalent alcohol is also preferably used as a pharmaceutically acceptable vehicle. The fatty acid ester may preferably be an ester of C8-20 fatty acid and a C2-3 monovalent alcohol, such as isopropyl myristate, isopropyl palmitate, ethyl linoleate and ethyl oleate.

Examples of polyols may preferably include alcohols having two or three hydroxy groups such as glycerin, polyethylene glycol and propylene glycol.

According to the present invention, the mixture which is filled in the soft-gelatin capsule shell may be obtained by dissolving or dispersing the above-described 15-keto-prostaglandin compound in the above described pharmaceutically acceptable vehicle which is liquid at the room temperature. When it is difficult to dissolve the 15-keto-PG compound directly in the vehicle, each of them may be dissolved in a solvent in which both of them are soluble respectively, and then the solutions may be combined.

The amount of the solvent in the mixture relative to the amount of the 15-keto-PG compound is not limited as long as the 15-keto-PG is stable in the final formulation. In general, the amount of the vehicle per one part of the 15-keto-PG compound may be 1-5,000,000, preferably, 5-1,000,000 and most preferably, 10-500,000 parts by weight.

The mixture used in the invention may further comprise an oil solvent such as mineral oil, liquid paraffin, and tocopherol. The mixture of the present invention may further comprise another pharmaceutically active ingredient.

In a preferred embodiment, the composition of the present invention is substantially free of water. The term "substantially free of water" means that the composition does not contain water that is intentionally added. It is understood that many materials contain water that is taken up from the atmosphere or is present as a coordination complex in its normal state. Water taken up by hygroscopic materials or present as a hydrate is permissibly present in the compositions of this embodiment. According to the embodiment, any water that is present in the composition should not be present in amounts such that the water will have a deleterious effect to the composition of the present invention.

According to the present invention, the shell of the soft gelatin capsule is manufactured from gelatin and a sugar alcohol as a plasticizer.

Sugar alcohol used in the present invention is an alcohol obtained by hydrogen reduction of the aldehyde group of a saccharide. For example, sorbitol, mannitol, maltitol, lactitol, palatinit, xylitol, erithyritol, sugar alcohol solution derived from corn starch, i.e. a mixture of sorbitol, sorbitan, mannitol and hydrogenated starch hydrolysate, hydrogenated maltose starch syrup, i.e. a mixture of maltitol, sorbitol and oligosaccharide alcohol. Preferred sugar alcohols may include sorbitol, maltitol, sugar alcohol solution derived from corn starch and hydrogenated maltose starch syrup. Especially, sugar alcohol solution derived from corn starch and available on market under the name "Anidrisorb™" or "Polysorb™" is preferably used.

According to the invention, the amount of the sugar alcohol used for preparing the shell of the soft gelatin capsule is not specifically limited as long as the physical properties of the resulting capsule is not deteriorated. In general, the amount of sugar alcohol plasticizer is 20 to 60 parts by weight, preferably, 30 to 50 parts by weight per 100 parts by weight of gelatin.

The soft gelatin capsule formulation of the 15-keto-PG compound may be manufactured according to a conventional manner using the above described liquid mixture and a mixture of gelatin and the plasticizer.

The present invention will be explained in more detail by means of the following examples, which are illustrated by way of example only and never intended to limit the scope of the present invention.

Reference Example 1

Compound 1 was dissolved in a vehicle shown in table 1 below to give 240 µg/g solution (sample). The precise concentration of compound 1 in the sample was determined by means of HPLC (day 0). Then, the sample was put in a hard grass container and kept at 55° C. for 10 days, and then the precise concentration of the compound 1 in the sample was determined by means of HPLC (day 10).

Compound 1

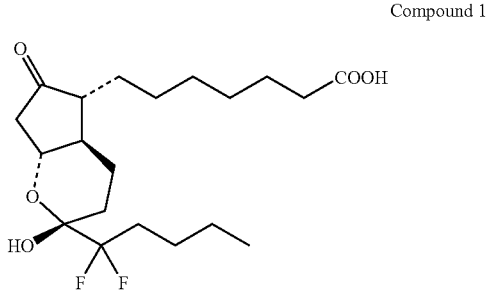

The determination of the concentration of the compound in the sample was carried out as follows. About 0.2 g of the sample was mixed with exactly 2 ml of internal standard solution and then with a dissolving agent shown in Table 1 to give 5 mL of sample solution. About 12 mg of the reference standard compound 1 was weighted precisely and added with acetonitrile to give exactly 100 ml solution. Exactly 0.8 ml of the solution was obtained and added with exactly 4 ml of the internal standard solution, and then added with the dissolving agent to give 10 ml of standard solution.

The fluorescent labeling agent was added to the respective solution, stirred and stood at room temperature. Then, respective solution in an amount that theoretically gives 3-6 ng of compound 1 was loaded on the column and analyzed under the condition as follows:

HPLC Analysis Condition:
Column; 5 mm×25 cm stainless steel column packed with octadecylsilane treated silica gel for HPLC (5 µm)
Mobile phase: mixture of acetonitrile HPLC grade: methanol HPLC grade: ammonium acetate (0.05 mol/L)
Temperature: 35° C.
Detector: spectrophotofluorometer
Results are shown in Table 1:

TABLE 1

Assay results of compound 1 after 55° C. storage

| | vehicle | dissolving agent | concentration of compound 1[1] day 0 | day 10 |
|---|---|---|---|---|
| 1 | hydrogenated maltose starch syrup | acetonitrile/ Water (1:1) | — | 24.4% |
| 2 | Sugar alcohol solution derived from corn starch[2] | methanol | — | 26.2% |
| 3 | glycerin | methanol | 92.0% | 78.0% |
| 4 | propylene glycol | acetonitrile | 97.8% | 88.6% |
| 5 | polyethylene glycol 400 | acetonitrile | 98.2% | 90.1% |

[1] Percentage based on a theoretical amount (240 µg/g)
[2] Polysorb 85/70/00 ™, ROQUETTE AMERICA, Inc.

Example 1

One hundred (100) parts by weight of gelatin (type A, high bloom, SKW Biosystems #195F) and 35 parts by weight of a plasticizer shown in Table 2 were mixed in water and dried to give gelatin piece. Compound 1 was dissolved in medium chain fatty acid triglyceride (USP/NF grade) to give a liquid mixture comprising 60 µg/g of the compound. 0.5 g of the liquid mixture and 0.5 g of each gelatin piece were put together in a sealed container and kept at 40° C. for 21 days. Then, the concentration of compound 1 contained in the liquid mixture was determined in the same manner as Reference Example 1. Results are shown in Table 2:

TABLE 2

Stability data of compound 1/medium chain fatty acid triglyceride (MCT) solution (60 µg/g)

| | gelatin piece | | concentration of compound 1 |
|---|---|---|---|
| plasticizer | | water content (after dried) | after storage[1] |
| glycerin | | 23% | 86.8% |
| sugar alcohol solution derived from corn starch[2] | | 25% | 92.0% |

[1] Percentage based on a theoretical amount (60 µg/g)
[2] Polysorb 85/70/00 ™, ROQUETTE AMERICA, Inc.

According to the reference example 1, in case the 15-keto-prostaglandin compound of the invention and the sugar alcohol were contacted directly, stability of the compound was significantly lowered. In contrast, in case the 15-keto-PG compound was directly contacted with a polyol such as glycerin, the stability of the compound was maintained. It have surprisingly revealed by Example 1 that the stability of the 15-keto-prostaglandin contacted with gelatin piece prepared using sugar alcohol as a plasticizer was better than that contacted with gelatin piece with glycerin as a plasticizer.

Example 2

Sugar alcohol solution derived from corn starch in an amount shown in Table 3 was added in an appropriate amount of water, stirred and heated. Then, gelatin 100 parts by weight was added thereto to give gelatin solution. Compound 1 was dissolved in medium chain fatty acid triglyceride (USP/NF grade) to give a fill solution containing 240 μg/g of compound 1. The gelatin solution and the liquid mixture were loaded or capsule forming and filling machine to give capsule containing the fill solution therein, and the capsule was dried to give soft gelatin capsule.

The capsule was put in a sealed container and kept at 40° C. for 3 months. The concentration of compound 1 in the fill solution contained in the capsule was determined after 1, 2 and 3 months storage in the same manner as Reference Example 1.

TABLE 3

Stability of soft gelatin capsule of compound 1

| soft gelatin capsule | | | conc. (% of Initial) 40° C. | | |
|---|---|---|---|---|---|
| (parts by weight) | | | 1 mo | 2 mo | 3 mo |
| gelatin | 100 | sugar | 35 | 99.9% | 100.3% | 99.2% |
| | | alcohol | 45 | — | 100.5% | 100.0% |
| | | solution[1)] | 55 | — | 99.3% | 100.0% |

[1)]Polysorb 85/70/00 ™, ROQUETTE AMERICA, Inc., derived from corn starch

What is claimed is:

1. A soft gelatin capsule formulation of a 15-keto-prostaglandin compound, which comprises:
   a soft gelatin capsule shell comprising gelatin and a sugar alcohol as a plasticizer, and
   a mixture comprising a 15-keto-prostaglandin compound and a pharmaceutically acceptable vehicle, which is filled in the shell.

2. The formulation of claim 1, wherein the 15-keto-prostaglandin compound is a compound of the formula (I):

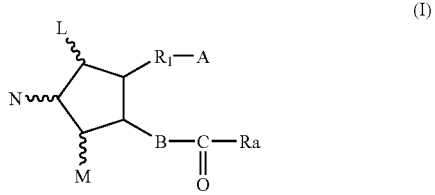

wherein L, M and N are hydrogen, hydroxy, halogen, lower alkyl, hydroxy(lower)alkyl, lower alkanoyloxy or oxo, wherein at least one of L and M is a group other than hydrogen, and the five-membered ring may have at least one double bond;

A is —$CH_3$, or —$CH_2OH$, —$COCH_2OH$, —COOH or a functional derivative thereof;

B is —$CH_2$—$CH_2$—, —CH=CH— or —C≡C—;

$R_1$ is a saturated or unsaturated bivalent lower or medium aliphatic hydrocarbon residue, which is unsubstituted or substituted with halogen, lower alkyl, hydroxy, oxo, aryl or heterocyclic group, and at least one of carbon atom in the aliphatic hydrocarbon is optionally substituted by oxygen, nitrogen or sulfur; and Ra is a saturated or unsaturated lower or medium aliphatic hydrocarbon residue, which is unsubstituted or substituted with halogen, oxo, hydroxy, lower alkyl, lower alkoxy, lower alkanoyloxy, cyclo(lower)alkyl, cyclo(lower)alkyloxy, aryl, aryloxy, heterocyclic group or heterocyclicoxy group; lower alkoxy; lower alkanoyloxy; cyclo(lower)alkyl; cyclo(lower)alkyloxy; aryl; aryloxy; heterocyclic group; heterocyclicoxy group.

3. The formulation of claim 1, wherein the 15-keto-prostaglandin compound is a 13,14-dihydro-15-keto-prostaglandin compound.

4. The formulation of claim 1, wherein the 15-keto-prostaglandin compound is a 15-keto-16-mono or 16,16-di-halogen-prostaglandin compound.

5. The formulation of claim 1, wherein the 15-keto-prostaglandin compound is a 13,14-dihydro-15-keto-16-mono- or 16,16-di-halogen-prostaglandin compound.

6. The formulation of claim 1, wherein the 15-keto-prostaglandin compound is a 15-keto-16-mono- or 16,16-di-fluoro-prostaglandin compound.

7. The formulation of claim 1, wherein the 15-keto-prostaglandin compound is a 13,14-dihydro-15-keto-16-mono- or 16,16-di-fluoro-prostaglandin compound.

8. The formulation of claim 1, wherein the 15-keto-prostaglandin compound is a 15-keto-prostaglandin E compound.

9. The formulation of claim 1, wherein the 15-keto-prostaglandin compound is a 13,14-dihydro-15-keto-16,16-difluoro-prostaglandin $E_1$.

10. The formulation of claim 1, wherein the 15-keto-prostaglandin compound is a 13,14-dihydro-15-keto-16,16-difluoro-18S-methyl-prostaglandin $E_1$.

11. The formulation of claim 1, wherein the sugar alcohol is selected from the group consisting of sorbitol, maltitol, sugar alcohol solution derived from corn starch, hydrogenated maltose syrup and a mixture thereof.

12. The formulation of claim 1, wherein the sugar alcohol comprises sorbitol and sorbitan as its major component.

13. A method for stabilizing a 15-keto-prostaglandin compound, which comprises: dissolving, dispersing or mixing the 15-keto-prostaglandin in a pharmaceutically acceptable vehicle to give a liquid mixture, and incorporating the liquid mixture in a soft gelatin capsule which comprises gelatin and a sugar alcohol as a plasticizer such that a soft gelatin capsule formulation of claim 1 is prepared.

14. A method for stabilizing a 15-keto-prostaglandin compound, which comprises encapsulating the compound together with a glyceride in a soft gelatin capsule shell comprising gelatin and a sugar alcohol as a plasticizer such that a soft gelatin capsule formulation of claim 1 is prepared.

15. The formulation of claim 1, wherein the pharmaceutically acceptable vehicle is a medium chain fatty acid triglyceride.

16. The method of claim 14, wherein the glyceride is a medium chain fatty acid triglyceride.

17. The formulation of claim 1, wherein the pharmaceutically acceptable vehicle is a fatty acid ester or a polyol.

18. The formulation of claim 1, wherein the pharmaceutically acceptable vehicle is glycerin or propylene glycol.

19. The formulation of claim 1, wherein the pharmaceutically acceptable vehicle is a fatty acid ester or glycerin.

20. The formulation of claim 1, wherein the pharmaceutically acceptable vehicle is a glyceride.

21. The formulation of claim 1, wherein the pharmaceutically acceptable vehicle is a fatty acid ester.

22. The formulation of claim 1, wherein the pharmaceutically acceptable vehicle is glycerin.

* * * * *